United States Patent [19]

Ikekawa et al.

[11] Patent Number: 5,278,155
[45] Date of Patent: Jan. 11, 1994

[54] FLUORINE-CONTAINING VITAMIN $D_3$ ANALOGUES AND CELL DIFFERENTIATION-INDUCING AGENT CONTAINING THE SAME

[75] Inventors: Nobuo Ikekawa, Musashino; Yoshiro Kobayashi, Tokyo, both of Japan; Yoko Tanaka, Delmar, N.Y.; Tadashi Eguchi, Tokyo, Japan

[73] Assignee: Daikin Industries, Ltd., Osaka, Japan

[21] Appl. No.: 710,394

[22] Filed: Jun. 5, 1991

[51] Int. Cl.$^5$ .......................... A61K 31/59; C07J 7/00
[52] U.S. Cl. ..................................... 514/167; 552/653
[58] Field of Search ................. 552/653; 514/167, 168

[56] References Cited

U.S. PATENT DOCUMENTS 4,853,378  8/1989  Hamma et al. ...................... 514/167

OTHER PUBLICATIONS

*The Lancet,* Colston et al., Jan. 28, 1989, pp. 188–191.
*Proc. Natl. Acad. Sci. USA,* Ostrem et al., vol. 84, pp. 2610–2614, May 1987.
*Bone Mineral Res.,* Stern et al., vol. 4, 3228, 1989.
Tanaka, et al., *Arch. Biochem. Biophys.,* vol. 29(1), pp. 348–354, Feb. 15, 1984.
Kiriyama, et al., *Endocrinology,* vol. 128(1), pp. 81–86, 1991.
Inaba, et al., *Arch. Biochem Biophys.,* vol. 268(1), pp. 35–39, Jan. 1989.

*Primary Examiner*—Marianne M. Cintins
*Assistant Examiner*—Kimberly J. Kestler
*Attorney, Agent, or Firm*—Birch, Stewart, Kolasch & Birch

[57] ABSTRACT

Fluorine-containing vitamin $D_3$ analogues of the formula [I]:

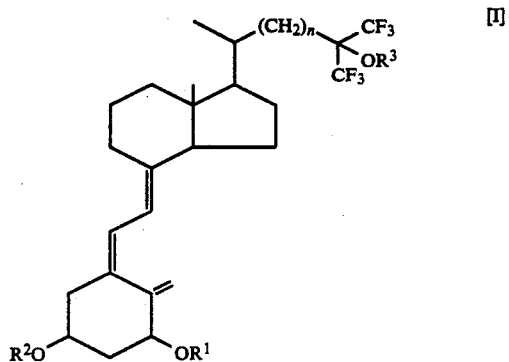

wherein $R^1$, $R^2$ and $R^3$ are independently hydrogen atom, a chemically inactive hydroxy-protecting group, an acyl having 2 to 8 carbon atoms or an alkyl having 1 to 8 carbon atoms, and n is an integer of 4 to 6, which have excellent pharmacological activities, particularly anti-tumor activity owing to differentiation-inducing activity and are useful for the prophylaxis and treatment of various tumors and intermediates therefore.

5 Claims, No Drawings

FLUORINE-CONTAINING VITAMIN $D_3$ ANALOGUES AND CELL DIFFERENTIATION-INDUCING AGENT CONTAINING THE SAME

This invention relates to novel fluorine-containing vitamin $D_3$ analogues having excellent pharmacological activities, particularly anti-tumor activity due to a differentiation-inducing activity capable of including tumor cells (e.g. colonic cancer cells) into normal cells, and a pharmaceutical composition having that differentiation-inducing activity which contains the fluorine-containing vitamin $D_3$ analogue as an active ingredient.

PRIOR ART

It is known that a bio-metabolite of vitamin $D_3$, $1\alpha,25$-dihydroxyvitamin $D_3$ referred to as "active-type vitamin $D_3$" and has an activity of promoting absorption of calcium via intestinal tract and is thus useful as a medicament for the treatment of bone diseases. Recently, it has been found that the active-type vitamin $D_3$ and analogues thereof possess a differentiation-inducing activity for recovering normal cells from cancerous cells (cf. Hirobumi Tanaka et al., "Seikagaku" (Biochemistry), Vol. 55, 1323, 1983) and further that some of these compounds have a remarked activity of inhibiting the progress of cancer (K. W. Colton et al., Lancet, Jan. 28, 188, 1989). However, in order to exhibit the differentiation-inducing activity, those compound should be used in amounts as large as 100 times the amount used ($10^{-9}-10^{-10}$M) for exhibiting the vitamin $D_3$ activities, and hence such compounds are not necessarily suitable for the treatment of leukemia and other cancers.

It has also been reported that 24-homo-$1\alpha,25$-dihydroxyvitamin $D_3$ and 24,24-bishomo analogues thereof, which have one longer carbon chain than the natural $1\alpha,25$-dihydroxyvitamin $D_3$, may also be usable as an anti-tumor drug (cf. V. K. Ostrem et al., Proc. Natl. Acad. Sci., 84, 2610, 1987, and P. Stern et al., . Bone Mineral Res., 4, s-228, 1989). However, these vitamin $D_3$ analogues are still not sufficiently used as anti-tumor drug. It is also described in WO 83/00335 (PCT/US82/00909) that some vitamin $D_3$ analogues such as 26,26,26,27,27,27-hexafluoro-$1\alpha,25$-dihydroxyvimin $D_3$ of the following formula have high vitamin D-like activities.

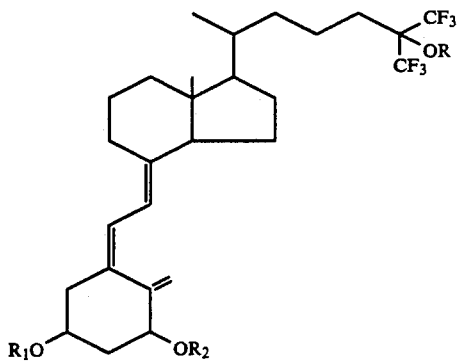

wherein R, $R_1$ and $R_2$ are independently hydrogen atom or an acyl having 1 to 4 carbon atoms.

SUMMARY DESCRIPTION OF THE INVENTION

The present inventors have intensively studied novel vitamin $D_3$ analogues which have been found to possess excellent pharmacological activities, particularly cell differentiation-inducing activity, and have found that some fluorine-containing vitamin $D_3$ have the desired properties.

An object of the invention is to provide novel fluorine-containing vitamin $D_3$ analogues having high cell differentiation-inducing activity. Another object of the invention is to provide a pharmaceutical composition suitable as a cell differentiation-inducing agent and which contains as an active ingredient the fluorine-containing vitamin $D_3$ analogue. A further object of the invention is to provide a novel intermediate suitable for the preparation of the active fluorine-containing vitamin $D_3$ analogues. These and other objects and advantages of the invention will be apparent to the skilled persons in this field from the following description.

DETAILED DESCRIPTION OF THE INVENTION

The fluorine-containing vitamin $D_3$ analogues of this invention are hexafluoro-$1\alpha,25$-dihyroxyvitamin $D_3$ derivatives of the formula [I]:

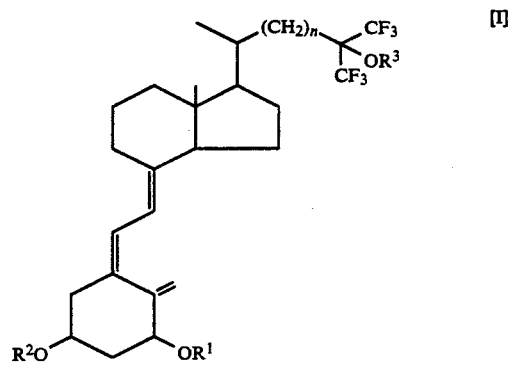

wherein $R^1$, $R^2$ and $R^3$ are independently hydrogen atom, a chemically inactive hydroxy-protecting group, an acyl having 2 to 8 carbon atoms, or an alkyl having 1 to 8 carbon atoms, and n is an integer of 4 to 6.

In the present specification and claims, the chemically inactive hydroxy-protecting group denotes a group being capable of forming acetal-like group (e.g. methoxymethyl, methoxyethoxymethyl, tetrahydropyranyl, etc.), a silyl ether type protecting group (e.g. trimethylsilyl, t-butyldimethylsilyl, t-butyldiphenylsilyl, etc.), and the like, among which t-butyldimethylsilyl is particularly preferable, but is not limited thereto. The acyl having 2 to 8 carbon atoms includes an alkanoyl having 2 to 8 carbon atoms and having optionally a halogen substituent (e.g. acetyl, chloroacetyl, propionyl, pivaloyl, etc.), an aromatic acyl having 7 to 8 carbon atoms and having optionally a halogen or nitro substituent (e.g. benzoyl, p-chlorobenzoyl, p-nitrobenzoyl, etc.), among which acetyl and benzoyl are particularly preferable, but it is not limited thereto. The alkyl having 1 to 8 carbon atoms includes straight chain or branched chain alkyl groups having 1 to 8 carbon atoms (e.g. methyl, ethyl, propyl, isopropyl, n-butyl, t-butyl, n-pentyl, n-hexyl, n-octyl, etc.) and alkyl groups substituted by an aromatic group such as a phenyl having optionally a substituent selected from a halogen and an alkyl having 1 to 4 carbon atoms (e.g. benzyl, p-chlorobenzyl, p-methoxybenzyl, etc.).

Suitable examples of the compounds [I] are as follows.

24-Homo-26,26,26,27,27,27-hexafluoro-1α,25-dihydroxyvitamin $D_3$ (Compound A)

24,24-Bishomo-26,26,26,27,27,27-hexafluoro-1α,25-dihydroxyvitamin $D_3$ (Compound B)

The compounds [I] of this invention can be prepared by various processes. One of the best processes is illustrated below.

A cholestane-5,7-diene of the formula [II]:

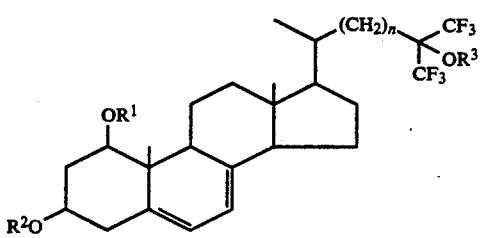

wherein $R^1$, $R^2$, $R^3$ and n are as defined above, is irradiated with ultraviolet radiation to give a pre-vitamin $D_3$ compound of the formula [III]:

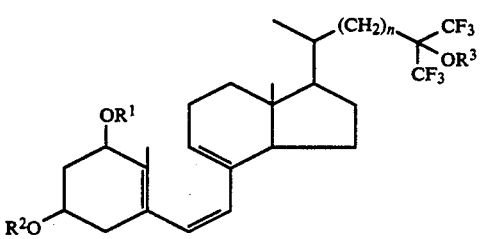

wherein $R^1$, $R^2$, $R^3$ and n are as defined above, subjecting the compound [III] to thermal isomerization to give the vitamin $D_3$ compound of the formula [I], and when $R^1$, $R^2$ and $R^3$ are each a chemically inactive hydroxy-protecting group or an acyl having 2 to 8 carbon atoms, optionally followed by removing the hydroxy-protecting group or the acyl group in the compound [I] to give a compound of the formula [IV]:

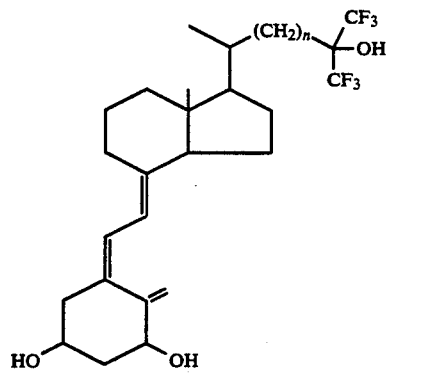

wherein n is as defined above.

The ultraviolet irradiation in the above process is usually carried out in an appropriate solvent such as aromatic hydrocarbons (e.g. benzene, toluene, etc.), lower alcohols (e.g. methanol, ethanol, etc.), aliphatic hydrocarbons (e.g. n-hexane, etc.), ethers (e.g. diethyl ether, tetrahydrofuran, etc.), or a mixture thereof, under an inert gas atmosphere such as nitrogen gas, or argon gas. The ultraviolet source includes any conventional one, for example mercury lamp, and if necessary, a filter may be used. The irradiation is usually carried out at a temperature of $-20°$ C. to 40° C., preferably $-10°$ C. to 20° C. The irradiation period of time may vary depending on the kinds of ultraviolet source, concentration of the starting compound [II], kind of the solvent, and the like, but is usually in the range of from several minutes to several tens of minutes.

The previtamin $D_3$ of the formula [III] obtained by the above ultraviolet irradiation can be isolated by a conventional method, for example, by distilling off the solvent and then subjecting to a conventional separation method such as chromatography, but it may be used in the next step without isolation. That is, the reaction mixture may be heated subjecting it to thermal isomerization. Thus, the reaction mixture obtained by the ultraviolet irradiation is heated at 20° C. to 120° C., preferably 50° C. to 100° C., for about 1 to 5 hours, by which the desired isomerization is effected. This thermal isomerization is preferably carried out under an inert gas atmosphere such as nitrogen gas or argon gas. After distilling off the solvent, the produced compound [I] is isolated by a conventional method such as chromatography.

When the compound [I] thus obtained is an ester compound, i.e. $R^1$, $R^2$ or $R^3$ being an acyl group, it may optionally be subjected to de-acylation to give a 24-homo derivative of 26,26,26,27,27,27-hexafluoro-1α,25-dihydroxyvitamin $D_3$ [IV]. The de-acylation is carried out by a conventional method, for example, by treating the ester compound with an alkali in a lower alcohol (e.g. methanol, ethanol, etc.), or with a metal hydride complex (e.g. lithium aluminum hydride, etc.) in an inert solvent (e.g. diethyl ether, tetrahydrofuran, etc.), at a temperature of $-20°$ C. to 50° C., usually at room temperature.

When the compound [I] obtained above has a chemically inactive hydroxy-protecting group, the removal of the hydroxy-protecting group from the compound [I] can be carried out by a conventional method. For example, in the case of a t-butyldimethylsilyl protecting group, the protected compound [I] is treated with a silyl ether cleaving agent (e.g. tetra-n-butylammonium fluoride, etc.) in an inert solvent (e.g. a cyclic ether, preferably tetrahydrofuran) at a temperature of from $-20°$ C. to 50° C., usually at room temperature.

The starting compound [II] used in the above reaction as well as the intermediates [III] and [IV] are all novel compounds. Thus, another object of this invention is to provide these novel starting material and intermediates.

The compound [II] may be prepared by various processes but is advantageously prepared by the following process. As one of the best embodiments, a process for preparing a compound of the formula [II] wherein $R^1$ and $R^2$ are acetyl, $R^3$ is hydrogen atom and n is 4, that is, 1α,3β-diacetoxy-24-homo-26,26,26,27,27,27-hexafluoro-cholesta-5,7-diene [IIa], and a compound of the formula [II] wherein $R^1$, $R^2$ and $R^3$ are all hydrogen atom and n is 4, that is 1α,3β-dihydroxy-24-homo-26,26,26,27,27,27-hexafluoro-cholesta-5,7-diene [IIb] is illustrated by the following reaction scheme:

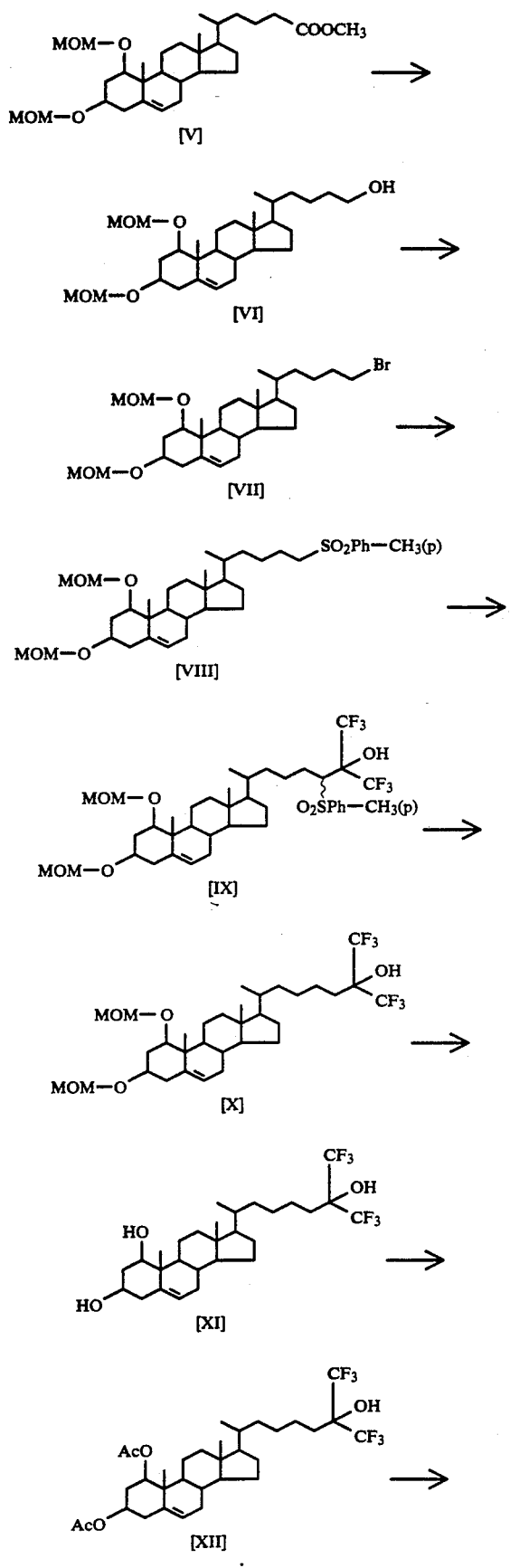

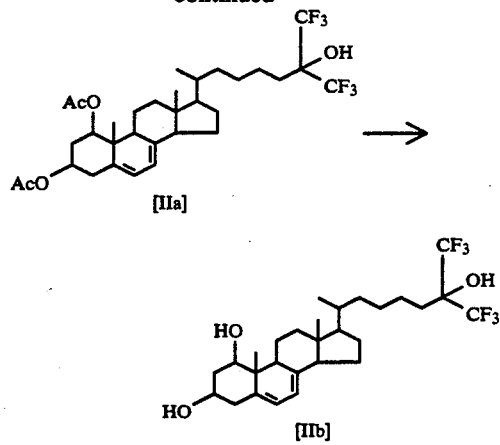

wherein MOM means methoxymethyl, Ph means phenyl and Ac means acetyl.

The other intermediates of the formulae [VI] to [XII] obtained in the above process are also novel.

The process is explained in more detail below.

The starting ester compound [V], which is prepared by the process as disclosed in Y. Kobayashi et al., *Chem. Pharm. Bull.*, Vol. 30, 4297, 1982, is reduced with a conventional reducing agent (e.g. lithium aluminum hydride) to give an alcohol [VI], and the alcohol [VI] is tosylated by a conventional method, for example by treating it with p-toluenesulfonyl chloride in pyridine, followed by reacting with a metal halide (e.g. lithium bromide) in an inert solvent (e.g. dimethylformamide) with heating to give a halide compound (e.g. bromide compound) [VII]. The halide compound [VII] is then converted into the corresponding arylsulfonyl compound [VIII] by reacting it with an arylsulfinate (e.g. sodium p-toluenesulfinate) in an appropriate inert solvent.

The arylsulfonyl compound [VIII] is converted into the compound [IX], for example, by previously converting the arylsulfonyl compound [VIII] into a carbanion compound by treating it with an alkyl-lithium (e.g. n-butyl-lithium, lithium-diisopropylamide), and then reacting the carbanion with trifluoroacetone.

The compound [IX] is obtained in the form of a mixture of epimers at 24-homo-positions of the side chain. The compound [IX] is treated with an alkali metal or an alkali metal amalgam in the presence of an alkali metal phosphate in an inert solvent such as a lower alkanol, a cyclic ether or a mixture thereof, by which the arylsulfonyl group is removed. The preferred reactant is sodium amalgam and disodium hydrogen phosphate. The preferred solvent is methanol, tetrahydrofuran, or a mixture thereof. The above reaction is preferably carried out by adding the alkali metal amalgam to the mixture of the compound [IX] in an inert solvent with stirring at −20° C. to 50° C., preferably 0° C. to 30° C., for 1 to 5 hours, preferably 2 to 3 hours. The protecting groups at 1- and 3-positions of the resultant compound [X] can be removed by treating it with an organic or inorganic acid (e.g. acetic acid, hydrochloric acid, or a mixture thereof) in an inert solvent (e.g. cyclic ethers, preferably tetrahydrofuran) to give the compound [XI]. This compound [XI] is then acetylated with a conventional process, for example, acetylated with acetic anhydride in pyridine to give the 1,3-diacetate compound [XII].

The 1,3-diacetate compound [XII] is converted into the desired 5,7-diene compound [IIa] by a conventional method, for example, by treating it with N-bromosuccinimide to introduce bromo group at 7-position, followed by removing HBr with a basic substance (e.g. tetra-n-butylammonium fluoride). The compound [IIa] is optionally deacetylated by a conventional method, for example, by hydrolyzing with an alkali or by reducing with a metal hydride complex (e.g. lithium aluminum hydride) to give the compound [IIb]. These compounds [IIa] and [IIb] can be purified by a conventional purification method, for example, by silica gel chromatography.

Another representative compound of the formula [II] wherein $R^1$ and $R^2$ are both acetyl, $R^3$ is hydrogen atom and n is 5, that is, $1\alpha,3\beta$-diacetoxy-24,24-bishomo-26,26,26,27,27, 27-hexafluoro-cholesta-5,7-diene [IIc] and compound [II] wherein $R^1$, $R^2$ and $R^3$ are hydrogen atom and n is 5, that is, $1\alpha,3\beta$-dihydroxy-24,24-bishomo-26,26,26,27,27,27-hexafluorocholesta-5,7-diene [IId] are prepared by the process illustrated by the following reaction scheme:

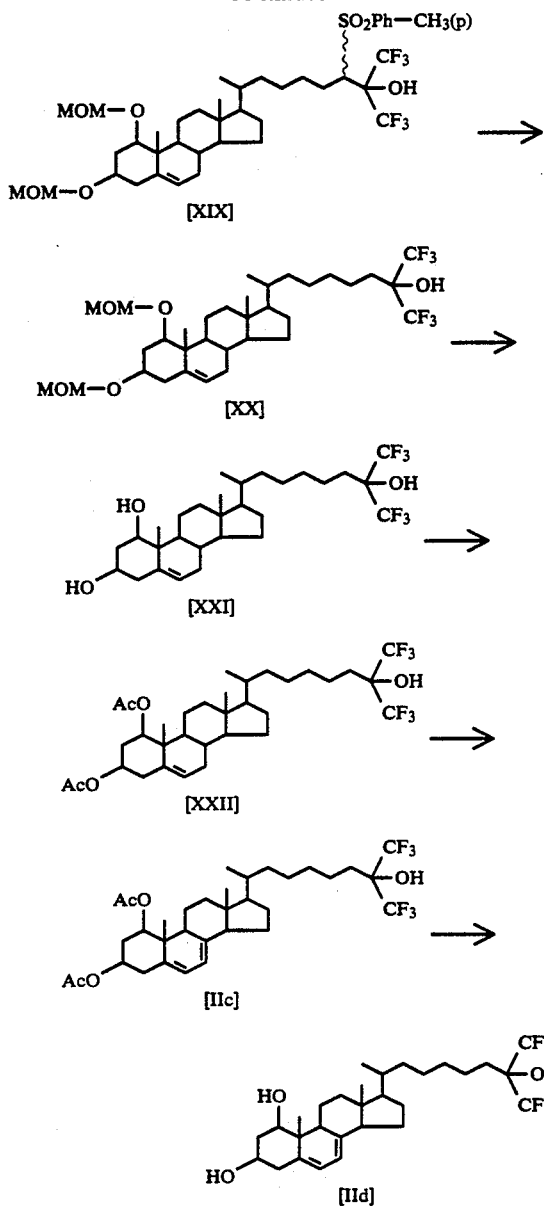

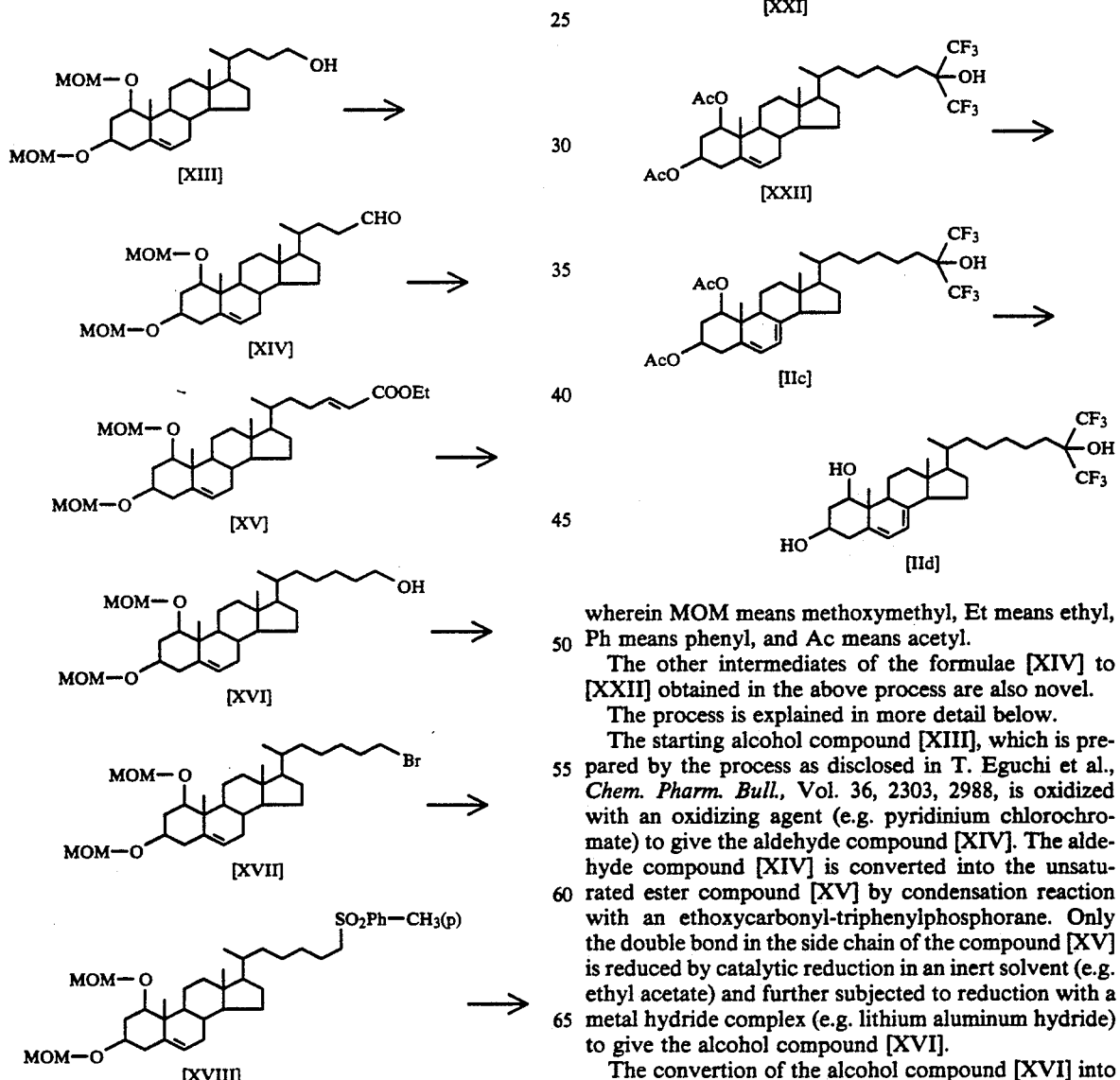

wherein MOM means methoxymethyl, Et means ethyl, Ph means phenyl, and Ac means acetyl.

The other intermediates of the formulae [XIV] to [XXII] obtained in the above process are also novel.

The process is explained in more detail below.

The starting alcohol compound [XIII], which is prepared by the process as disclosed in T. Eguchi et al., Chem. Pharm. Bull., Vol. 36, 2303, 2988, is oxidized with an oxidizing agent (e.g. pyridinium chlorochromate) to give the aldehyde compound [XIV]. The aldehyde compound [XIV] is converted into the unsaturated ester compound [XV] by condensation reaction with an ethoxycarbonyl-triphenylphosphorane. Only the double bond in the side chain of the compound [XV] is reduced by catalytic reduction in an inert solvent (e.g. ethyl acetate) and further subjected to reduction with a metal hydride complex (e.g. lithium aluminum hydride) to give the alcohol compound [XVI].

The convertion of the alcohol compound [XVI] into the desired 24,24-dihomo compounds [IIc] and [IId] can be carried out in the same manner as described above for the convertion of from the alcohol compound [VI] to the 24-homo compounds [IIa] and [IIb].

The fluorine-containing vitamin $D_3$ analogues [I] of this invention have excellent pharmacological activities, particularly anti-tumor activity due to their cell differentiation-inducing activity, and are useful as differentiation-inducing agents for the prophylaxis and treatment of various tumors.

The compounds [I] of this invention can be administered by conventional methods, conventional types of unit dosages or with a conventional pharmaceutical carrier or diluent to human beings and animals by oral route or parenteral route such as injections (e.g. intramuscular, subcutaneous, or intravenous injection), or by topical or external application.

For oral administration, the compounds [I] are usually formed in a conventional pharmaceutical preparation, in solid form such as tablets, capsules, granules, fine granules, powders, lozenge, troches, or in liquid form such as solutions, emulsions (e.g. water-in-oil type emulsions), suspensions or syrups. When formed into tablets or other solid preparations, one or more of the compounds [I] are admixture with conventional excipients (e.g. sodium citrate, lactose, microcrystalline cellulose, starch, etc.), lubricating agents (e.g. anhydrous silicic acid, hydrized castor oil, magnesium stearate, sodium lauryl sulfate, talc, etc.), binding agents (e.g. starch paste, glucose, lactose, gum acacia, gelatin, mannitol, etc.), and any other conventional additives such as flavors, colorants, preservatives including antioxidants, surfactants, dispersing agents, emulsifiers, and the like and the mixture is formed into the desired preparation in a conventional manner. For liquid preparations, conventional liquid carriers such as water, physiological saline solution, oil, etc. are used.

For parenteral administration, the compound [I] is used in a sterilized oily or aqueous preparation. Injection preparation is usually prepared by dissolving the active compound [I] in water for injection, if necessary, followed by buffering or making isotonic with glucose, saline, or the like. External preparation is preferably ointment but includes other preparations such as liniments, lotions, applications, emulsions (e.g. creams), solutions, suspensions, and the like. The ointment can be prepared by a conventional method with conventional ointment base containing fats, fatty oils (e.g. olive oil, sesame oil, medium fatty acid triglycerides, etc.), lanolin, wax, paraffin, glycols, higher alcohols, surfactants, and the like.

The dosage of the compound [I] of this invention may vary somewhat in accordance with the administration methods, sex and age of the patient, severity of disease, and the like, but is usually used in a dose of 0.1 to 200 $\mu$g per day, preferably 0.1 to 50 $\mu$g per day, in adult. The compound [I] of this invention may be used alone or together with other anti-tumor drug(s).

The compounds of this invention and preparation thereof are illustrated by the following Examples and Experiments, but should not be construed to be limited thereto.

Example 1

Preparation of $1\alpha,3\beta$-bis(methoxymethoxy)-26,27-dinor-25-hydroxy-cholest-5-ene (Compound VI):

$1\alpha,3\beta$-Bis(methoxymethoxy)-26,27-dinor-24-methoxycarbonyl-cholest-5-ene (Compound V) (1.8 g, 3.56 mmol) is dissolved in tetrahydrofuran (abbreviated as THF) (30 ml), and thereto are added lithium aluminum hydride (270 mg, 7.11 mmol), and the mixture is stirred at room temperature under nitrogen gas for 10 minutes. To the reaction mixture are added a small amount of ethyl acetate and further water. The mixture is extracted with ethyl acetate. The organic layer is washed with saline solution and dried over anhydrous sodium sulfate. After distilling off the solvent, the residue is purified by silica gel column chromatography (eluant: hexane-ethyl acetate=2:1) to give the title compound (VI) (1.6 g, 94%).

$^1$H-NMR (CDCl$_3$) $\delta$: 0.78 (3H, s, 18-H), 0.92 (3H, d, J=6Hz, 21-H), 1.05 (3H, s, 19-H), 3.36 (3H, s, OCH$_3$), 3.40 (3H, s, OCH$_3$), 3.65 (2H, t, J=7Hz, 25-H), 3.74 (1H, m, 1-H), 3.85 (1H, m, 3-H), 4.59 and 4.75 (2H, each d, J=7Hz, OCH$_2$O), 4.68 (2H, s, OCH$_2$O), 5.55 (1H, m, 6-H)

IR (neat): 3420 cm$^{-1}$

Elementary analysis for $C_{29}H_{50}O_5$: Calcd. (%): C,72.76; H,10.53 Found (%): C,72.86; H,10.35

Example 2

Preparation of $1\alpha,3\beta$-bis(methoxymethoxy)-25-bromo-26,27-dinor-cholest-5-ene (Compound VII):

The compound VI obtained in Example 1 (1.6 g, 3.34 mmol) is dissolved in pyridine (7.6 ml), and the mixture is cooled to 0° C. and thereto is added p-toluenesulfonyl chloride (1.3 g, 2 equivalents). The mixture is stirred at 0° C. for 3.5 hours and allowed to stand in refrigerator overnight. To the reaction mixture is added a piece of ice, and the mixture is sitrred for 10 minutes and extracted with ethyl acetate. The organic layer is washed with 2N hydrochloric acid, saturated sodium hydrogen carbonate solution, and saline solution in this order, and dried over anhydrous sodium sulfate. After distilling off the solvent, the residue is dissolved in dimethylformamide (abbreviated as DMF) (25 ml), and thereto is added lithium bromide (344 mg, 1.2 equivalent). The mixture is refluxed from 3.5 hours, cooled to room temperature and then extracted with ethyl acetate. After cooling to room temperature, the mixture is extracted with ethyl acetate. The organic layer is washed with saline solution and dried over anhydrous sodium sulfate. After distilling off the solvent, the residue is purified by silica gel column chromatography (eluant, hexane-ethyl acetate=8:1) to give the title compound (VII) (1.5 g, 83%).

$^1$H-NMR (CDCl$_3$) $\delta$: 0.69 (3H, s, 18-H), 0.88 (3H, d, J=6Hz, 21-H), 1.05 (3H, s, 19-H), 3.36 (3H, s, OCH$_3$), 3.40 (3H, s, OCH$_3$), 3.42 (2H, t, J=7Hz, 25-H), 3.74 (1H, m, 1-H), 3.86 (1H, m, 3-H), 4.58 and 4.75 (2H, each d, J=7Hz, OCH$_2$O), 4.68 (2H, s, OCH$_2$O), 5.56 (1H, m, 6-H)

IR (neat): 2930, 1460, 1040 cm$^{-1}$

Elementary analysis for $C_{29}H_{49}O_4Br$: Calcd. (%): C,64.31; H,9.12 Found (%): C,64,33; H,8.99

Example 3

Preparation of $1\alpha,3\beta$-bis(methoxymethoxy)-26,27-dinor-25-p-toluenesulfonyl-cholest-5-ene (Compound VIII):

The compound (VII) obtained in Example 2 (1.5 g, 2.8 mmol) is dissolved in DMF (20 ml), and thereto is added sodium p-toluenesulfinate (2.5 g, 5 equivalents), and the mixture is refluxed overnight. The reaction mixture is cooled to room temperature and extracted with ethyl acetate. The organic layer is washed with saline solution and dried over anhydrous sodium sulfate.

After distilling off the solvent, the residue is purified by silica gel column chromatography (eluant, hexane-ethyl acetate=6:1) to give the title compound (VIII) (1.3 g, 75%).

$^1$H-NMR (CDCl$_3$) δ: 0.67 (3H, s, 18-H), 0.87 (3H, d, J=6Hz, 21-H), 1.04 (3H, s, 19-H), 2.46 (3H, s, CH$_3$Ph), 3.07 (2H, t, J=8Hz, 25-H), 3.37 (3H, s, OCH$_3$), 3.40 (3H, s, OCH$_3$), 3.74 (1H, m, 1-H), 3.86 (1H, m, 3-H), 4.59 and 4.76 (2H, each d, J=7Hz, OCH$_2$O), 4.69 (2H, s, OCH$_2$O), 5.57 (1H, m, 6-H), 7.37 and 7.79 (4H, each d, J=9Hz, aromatic)

IR (neat): 1600, 1130 cm$^{-1}$

Elementary analysis for C$_{36}$H$_{56}$O$_6$S: Calcd. (%): C,70.09; H,9.15 Found (%): C,70,28; H,9.30

Example 4

Preparation of 1α,3β-bis(methoxymethoxy)-24-homo-26,26,26,27,27,27-hexafluoro-25-hydroxy-24-p-toluenesulfonyl-cholest-5-ene (Compound IX):

Dipyridyl (1 mg) and diisopropylamine (0.74 ml) are added to THF (5 ml), and the mixture is cooled to −78° C., and thereto is added n-butyl-lithium (3.4 ml, 1.55M), and the mixture is stirred at −78° C. for 10 minutes and further at 0° C. for 30 minutes. To the mixture is added a solution of the compound (VIII) obtained in Example 3 (1.30 g, 2.1 mmol) in THF (5 ml) at the same temperature. The mixture is stirred at −78° C. for one hour, and thereto is added a large excess amount of hexafluoroacetone gas at −78° C. After 30 minutes, water is added to the reaction mixture, and the mixture is extracted with ethyl acetate. The organic layer is washed with saturated ammonium chloride solution and saline solution in this order and dried over anhydrous sodium sulfate. After distilling off the solvent, the residue is purified by silica gel column chromatography (eluant, hexane-ethyl acetate=7:1) to give the title compound (IX) (1.30 g, 75%).

$^1$H-NMR (CDCl$_3$) δ: 0.64 (6H, m, 18-H and 21-H), 1.02 (3H, s, 19-H), 2.48 (3H, s, CH$_3$Ph), 3.37 (3H, s, OCH$_3$), 3.40 (3H, s, OCH$_3$), 3.49 (1H, m, 24'-H), 3.71 (1H, m, 1-H), 3.85 (1H, m, 3-H), 4.59 and 4.74 (2H, each d, J=7Hz, OCH$_2$O), 4.69 (2H, s, OCH$_2$O), 5.54 (1H, m, 6-H), 6.76 (1H, br.s, OH), 7.43 and 7.84 (4H, each d, J=9Hz, aromatic)

IR (neat): 3300, 1140 cm$^{-1}$

Elementary analysis for C$_{39}$H$_{56}$O$_7$SF$_6$: Calcd (%): C,59.82; H,7.21 Found (%): C,59,85; H,7.23

Example 5

Preparation of 1α,3β-bis(methoxymethoxy)-26,26,26,27,27,27-hexafluoro-24-homo-25-hydroxy-cholest-5-ene (Compound XI):

The compound (IX) obtained in Example 4 (1.2 g, 1.5 mmol) is dissolved in a mixture of THF (10 ml) and methanol (12 ml), and thereto is added disodium hydrogen phosphate (1.0 g) and 5% sodium amalgam (5.0 g). The mixture is stirred at room temperature for 2 hours. The insoluble materials are filtered off, and the filtrate is diluted with ethyl acetate, and the mixture is washed with saline solution and dried over anhydrous sodium sulfate. After distilling off the solvent, the residue is purified by silica gel column chromatography (eluant, hexane-ethyl acetate=7:1) to give the title compound (X) (711 mg, 75%).

$^1$H-NMR (CDCl$_3$) δ: 0.68 (3H, s, 18-H), 0.91 (3H, d, J=6Hz, 21-H), 1.02 (3H, s, 19-H), 3.35 (3H, s, OCH$_3$), 3.40 (3H, s, OCH$_3$), 3.73 (1H, m, 1-H), 3.84 (1H, m, 3-H), 4.28 (1H, br.s, OH), 4.59 and 4.75 (2H, each d, J=7Hz, OCH$_2$O), 4.64 (2H, s, OCH$_2$O), 5.55 (1H, m 6-H)

IR (neat): 3290 cm$^{-1}$

Elementary analysis for C$_{32}$H$_{50}$O$_5$SF$_6$: Calcd. (%): C,61.11; H,8.02 Found (%): C,61,03; H,8.14

Example 6

Preparation of 24-homo-26,26,26,27,27,27-hexafluoro-1α,3β,25-trihydroxy-cholest-5-ene (Compound XI):

The compound (X) obtained in Example 5 (656 mg, 1.04 mmol) is dissolved in THF (10 ml), and thereto are dark room at room temperature under argon gas for one hour. After adding further tetra-n-butylammonium fluoride (0.56 ml, as 1M solution in THF, 3.5 equivalents), the mixture is again stirred for 30 minutes. [This mixture contains compound (IIa) and it can be isolated by a conventional method in a yield of 151 mg (35%)]. The above reaction mixture is diluted with ethyl acetate, washed with saturated sodium hydrogen carbonate solution and saline solution in this order, and dried over anhydrous sodium sulfate. After distilling off the solvent, the residue is dissolved in THF (5 ml) and thereto is added 5% potassium hydroxide-methanol (2 ml). The mixture is stirred at room temperature under argon gas overnight. The reaction mixture is diluted with ethyl acetate, washed with saline solution and dried over anhydrous sodium sulfate. After distilling off the solvent, the residue is purified by silica gel column chromatography (eluant, hexane-ethyl acetate=2:1) to give the title compound (IIb) (23 mg, 26%).

UV λ$_{max}$: 294, 282, 272 nm $^1$H-NMR (CDCl$_3$) δ: 0.61 (3H, s, 18-H), 0.87 (3H, s, 19-H), 0.92 (3H, d, J=7Hz, 21-H), 3.73 (1H, m, 1-H), 3.92 (1H, m, 3-H), 5.29 and 5.57 (2H, m, 6- and 7-H)

Example 9

Preparation of 1α,25-dihydroxy-26,26,26,27,27,27-hexafluoro-24-homo-vitamin D$_3$ (Compound IV; n=4):

The compound (IIb) obtained in Example 8 (23 mg, added 6N hydrochloric acid (2 ml), and the mixture is stirred at 50° C. for 3.5 hours. The reaction mixture is diluted with ethyl acetate, washed with saturated sodium hydrogen carbonate solution and saline solution in this order, and dried over anhydrous sodium sulfate. After distilling off the solvent, the residue is purified by silica gel column chromatography (eluant, hexane-ethyl acetate=2:1) to give the title compound (XI) (465 mg, 83%). M.p. 166°-168° C. (recrystallized from acetone-hexane)

$^1$H-NMR (CDCl$_3$) δ: 0.68 (3H, s, 18-H), 0.92 (3H, d, J=6Hz, 21-H), 1.04 (3H, s, 19-H), 3.07 (1H, br.s, OH), 3.84 (1H, m, 1-H), 3.98 (1H, m, 3-H), 5.59 (1H, m 6-H)

IR (neat): 3400 cm$^{-1}$

Elementary analysis for C$_{28}$H$_{42}$O$_3$SF$_6$: Calcd. (%): C,62.20; H,7.83 Found (%): C,61,93; H,7.74

Example 7

Preparation of 1α,3β-diacetoxy-24-homo-26,26,26,27,27,27-hexafluoro-25-hydroxy-cholest-5-ene (Compound XII):

The compound (XI) obtained in Example 6 (411 mg, 0.76 mmol) is dissolved in pyridine (2 ml), and thereto is added acetic anhydride (0.4 ml), and the mixture is stirred at room temperature for two days. To the mixture is added a piece of ice, and the mixture is stirred for 10 minutes and extracted with ethyl acetate. The organic layer is washed with 2H hydrochloric acid, saturated sodium hydrogen carbonate solution and saline solution in this order and dried over anhydrous sodium sulfate. After distilling off the solvent, the residue is purified by silica gel column chromatography (eluant, hexane-ethyl acetate=2:1) to give the title compound (XII) (198 mg, 42%). M.p. 149°-150° C. (recrystallized from hexane-ethyl acetate)

$^1$H-NMR (CDCl$_3$) δ: 0.65 (3H, s, 18-H), 0.90 (3H, d, J=6Hz, 21-H), 1.09 (3H, s, 19-H), 2.03 (3H, s, COCH$_3$), 2.09 (3H, s, COCH$_3$), 4.91 (1H, m, 3-H), 5.06 (1H, m, 1-H), 5.53 (1H, m, 6-H)

IR (neat): 3250, 1720 cm$^{-1}$

Elementary analysis for C$_{32}$H$_{46}$O$_5$F$_6$: Calcd. (%): C,61.52; H,7.42 Found (%): C,61,80; H,7.31

Example 8

Preparation of 26,26,26,27,27,27-hexafluoro-24-homo-1α,3β,25-trihydroxy-cholesta-5,7-diene (Compound IIb):

The compound (XII) obtained in Example 7 (100 mg, 0.16 mmol) is dissolved in carbon tetrachloride (2 ml), and thereto is added N-bromosuccinimide (39.9 mg, 1.4 equivalent), and the mixture is refluxed under argon gas for 20 minutes. After the reaction mixture is ice-cooled, the insoluble substances are filtered off. After the filtrate is distilled to remove the solvent, the residue is dissolved in THF (5 ml) and thereto is added a catalytic amount of tetra-n-butylammonium bromide. The mixture is sitrred in a 0.04 mmol) is dissolved in a mixture of benzene (90 ml) and ethanol (40 ml), and the mixture is irradiated with ultraviolet by means of medium-pressure mercury lamp (Hanovia 654A, 200 W) at 0° C. under argon gas for 5 minutes. The solution is refluxed under argon gas for one hour. After distilling off the solvent, the residue is purified by thin layer chromatography (developer, benzene-ethyl acetate=3:1, five times developing, Rf=0.46) to give the title compound (IV) (1.15 mg, 5%).

UV λ$_{max}$: 265 nm, λ$_{min}$: 228 nm $^1$H-NMR (CDCl$_3$) δ: 0.55 (3H, s, 18-H), 0.92 (3H, d, J=6Hz, 21-H), 2.31 (1H, dd, J=13Hz and 7Hz, 4β-H), 2.60 (1H, dd, J=13Hz and 4 Hz, 4α-H), 2.82 (1H, dd, J=12Hz and 3Hz, 9β-H), 4.24 (1H, m, 3-H), 4.44 (1H, m, 1-H), 5.01 (1H, br.s, 19E-H), 5.33 (1H, br.s, 19Z-H), 6.03 (1H, d, J=11Hz, 7-H), 6.38 (1H, d, J=11Hz, 6-H)

Example 10

Preparation of 1α,3β-bis(methoxymethoxy)-chol-5-en-24-al (Compound XIV):

The compound (XIII) (2.2 g, 4.7 mmol) is dissolved in dichloromethane (40 ml), and thereto are added pyridinium chlorochromate (PCC) (2.3 g, 10.7 mmol) and molecular sieves 3A (5 g), and the mixture is stirred at room temperature under nitrogen gas for 2.5 hours. To the mixture is added diethyl ether (200 ml), and the mixture is filtered with a column packed with Florisil (activated magnesium silicate, 50 g). After the filtrate is distilled to remove the solvent, the residue is purified by silica gel column chromatography (eluant, hexane-ethyl acetate=4:1) to give the title compound (XIV) (1.6 g, 73%).

M.p. 95°-97° C. (recrystallized from acetone)

$^1$H-NMR (CDCl$_3$) δ: 0.68 (3H, s, 18-H), 0.92 (3H, d, J=6Hz, 21-H), 1.03 (3H, s, 19-H), 3.35 (3H, s, OCH$_3$), 3.40 (3H, s, OCH$_3$), 3.74 (1H, m, 1-H), 3.86 (1H, m, 3-H), 4.59 and 4.76 (2H, each d, J=7Hz, OCH$_2$O), 4.67 (2H, s, OCH$_2$O), 5.57 (1H, m, 6-H), 9.77 (1H, t, J=2Hz, CHO)

IR (CHCl$_3$) 1720 cm$^{-1}$

Elementary analysis for C$_{28}$H$_{46}$O$_5$: Calcd. (%): C,72.69; H,10.02 Found (%): C,72,46; H,10.21

Example 11

Preparation of ethyl 1α,3β-bis(methoxymethoxy)-27-nor-cholesta-5,24-dien-26-ate (Compound XV):

The compound (XIV) obtained in Example 10 (2.9 g, 6.3 mmol) is dissolved in benzene (20 ml), and thereto is added ethoxycarbonyl-triphenylphosphorane (4.4 g, 2.2 equivalents), and the mixture is stirred at room temperature under nitrogen gas for 3 hours. After the mixture is distilled to remove the solvent, the residue is purified by silica gel column chromatography (eluant, hexane-ethyl acetate=6:1) to give the title compound (XV) (2.7 g, 80%).

$^1$H-NMR (CDCl$_3$) δ: 0.68 (3H, s, 18-H), 0.94 (3H, d, J=6Hz, 21-H), 1.03 (3H, s, 19-H), 1.29 (3H, t, J=7Hz, CH$_2$CH$_3$), 3.35 (3H, s, OCH$_3$), 3.40 (3H, s, OCH$_3$), 3.75 (1H, m, 1-H), 3.85 (1H, m, 3-H), 4.18 (2H, q, J=7Hz, CH$_2$CH$_3$), 4.58 and 4.75 (2H, each d, J=7Hz, OCH$_2$O), 4.67 (2H, s, OCH$_2$O), 5.57 (1H, m, 6-H), 5.81 (1H, dt, J=16Hz and 1.5Hz, 25-H), 6.96 (1H, dt, J=16Hz and 7Hz, 24-H)

IR (neat): 1720 cm$^{-1}$

Elementary analysis for C$_{32}$H$_{52}$O$_6$: Calcd. (%): C,72.14; H,9.84 Found (%): C,72,27; H,9.97

Example 12

Preparation of 1α,3β-bis(methoxymethoxy)-26-hydroxy-27-nor-cholest-5-ene (Compound XVI):

The compound (XV) obtained in Example 11 (2.7 g, 5.1 mmol) is dissolved in ethyl acetate (50 ml), and thereto is added 5% palladium/carbon (250 mg), and the mixture is stirred at room temperature under hydrogen gas stream for 3 hours. The catalyst is filtered off with silica gel column and the eluted solution is concentrated. The residue is dissolved in THF (30 ml) and thereto is added lithium aluminum hydride (387 mg, 10.2 mmol), and the mixture is stirred at room temperature under nitrogen gas for 15 minutes. To the reaction mixture are added a small amount of ethyl acetate and further water. The mixture is extracted with ethyl acetate, and the organic layer is washed with saline solution and dried over anhydrous sodium sulfate. After distilling off the solvent, the residue is purified by silica gel column chromatography (eluant, hexane-ethyl acetate=2:1) to give the title compound (XVI) (2.2 g, 87%).

$^1$H-NMR (CDCl$_3$) δ: 0.69 (3H, s, 18-H), 0.91 (3H, d, J=6Hz, 21-H), 1.01 (3H, s, 19-H), 3.35 (3H, s, OCH$_3$), 3.40 (3H, s, OCH$_3$), 3.64 (2H, t, J=7Hz, 26-H), 3.75 (1H, m, 1-H), 3.85 (1H, m, 3-H), 4.59 and 4.75 (2H, each d, J=7Hz, OCH$_2$O), 4.67 (2H, s, OCH$_2$O), 5.16 (1H, m, 6-H)

IR (neat): 3400 cm$^{-1}$

Elementary analysis for C$_{30}$H$_{52}$O$_5$: Calcd. (%): C,73.12; H,10.64 Found (%): C,72,90; H,10.60

Example 13

Preparation of 1α,3β-bis(methoxymethoxy)-26-bromo-27-nor-cholest-5-ene (Compound XVII):

The compound (XVI) obtained in Example 12 (2.2 g, 4.47 mmol) is dissolved in pyridine (10 ml), and the mixture is cooled to 0° C. and thereto is added p-toluenesulfonyl chloride (1.7 g, 2 equivalents). The mixture is stirred at 0° C. for 2 hours and allowed to stand in a refrigerator overnight. After adding a piece of ice, the mixture is stirred for 10 minutes and extracted with ethyl acetate. The organic layer is washed with 2N hydrochloric acid, saturated sodium hydrogen carbonate solution and saline solution in this order and dried over anhydrous sodium sulfate. After distilling off the solvent, the residue (2.9 g) is dissolved in DMF (25 ml) and thereto is added lithium bromide (467 mg, 1.2 equivalent). The mixture is refluxed for 2.5 hours. After cooling to room temperature, the reaction mixture is extracted with ethyl acetate, and the organic layer is washed with saline solution and dried over anhydrous sodium sulfate. After distilling off the solvent, the residue is purified by silica gel column chromatography (eluant, hexane-ethyl acetate=9:1) to give the title compound (XVII) (2.2 g, 88%).

$^1$H-NMR (CDCl$_3$) δ: 0.70 (3H, s, 18-H), 0.90 (3H, d, J=6Hz, 21-H), 1.01 (3H, s, 19-H), 3.35 (3H, s, OCH$_3$), 3.39 (3H, s, OCH$_3$), 3.41 (3H, t, J=7Hz, 26-H), 3.74 (1H, m, 1-H), 3.86 (1H, m, 3-H), 4.59 and 4.75 (2H, each d, J=7Hz, OCH$_2$O), 4.67 (2H, s, OCH$_2$O), 5.55 (1H, m, 6-H)

IR (neat): 2900, 1440, 1030 cm$^{-1}$

Elementary analysis for C$_{30}$H$_{51}$O$_4$Br: Calcd. (%): C,64.85; H,9.25 Found (%): C,65,00; H,9.26

Example 14

Preparation of 1α,3β-bis(methoxymethoxy)-27-nor-26-p-toluenesulfonyl-cholest-5-ene (Compound XVIII):

The compound (XVII) obtained in Example 13 (2.2 g, 4.0 mmol) is dissolved in DMF (20 ml), and thereto is added sodium p-toluenesulfinate (3.6 g, 5 equivalents), and the mixture is refluxed overnight. After cooling to room temperature, the mixture is extracted with ethyl acetate. The organic layer is washed with saline solution and dried over anhydrous sodium sulfate. After distilling off the solvent, the residue is purified by silica gel column chromatography (eluant, hexane-ethyl acetate=4:1) to give the title compound (XVIII) (1.6 g, 62%).

$^1$H-NMR (CDCl$_3$) δ: 0.67 (3H, s, 18-H), 0.87 (3H, d, J=6Hz, 21-H), 1.03 (3H, s, 19-H), 2.46 (3H, s, CH$_3$Ph), 3.05 (2H, m, CH$_2$SO$_2$), 3.37 (3H, s, OCH$_3$), 3.41 (3H, s, OCH$_3$), 3.74 (1H, m, 1-H), 3.85 (1H, m, 3-H), 4.59 and 4.75 (2H, each d, J=7Hz, OCH$_2$O), 4.67 (2H, s, OCH$_2$O), 5.55 (1H, m, 6-H), 7.34 and 7.78 (4H, each d, J=9Hz, aromatic)

IR (neat): 1600, 1040 cm$^{-1}$

Elementary analysis for C$_{37}$H$_{58}$O$_6$S: Calcd. (%): C,70.44; H,9.27 Found (%): C,70,15; H,9.56

Example 15

Preparation of 1α,3β-bis(methoxymethoxy)-24,24-dihomo-26,26,26,27,27,27-hexafluoro-25-hydroxy-24-p-toluenesulfonyl-cholest-5-ene (Compound XIX):

Dipyridyl (1 mg) and diisopropylamine (0.56 ml) are added to THF (5 ml) and the mixture is cooled to −78° C. and thereto is added n-butyl-lithium (2.6 ml, 1.55 M). The mixture is stirred at −78° C. for 10 minutes and further at 0° C. for 30 minutes. To the mixture is added a solution of the compound (XVIII) obtained in Example 14 (843 mg, 1.3 mmol) in THF (5 ml) at the same temperature. The mixture is stirred at −78° C. for one hour, and thereto is introduced a large excess amount of hexafluoroactone gas at −78° C. After 30 minutes, water is added to the mixture, and the mixture is extracted with ethyl acetate. The organic layer is washed with saturated ammonium chloride solution and saline solution in this order and dried over anhydrous sodium sulfate. After distilling off the solvent, the residue is purified by silica gel column chromatography (eluant, hexane-ethyl acetate=7:1) to give the title compound (XIX) (1.05 g, 95%).

$^1$H-NMR (CDCl$_3$) δ: 0.64 (3H, s, 18-H), 0.80 (3H, m, 21-H), 1.02 (3H, s, 19-H), 2.49 (3H, s, CH$_3$Ph), 3.39 (3H, s, OCH$_3$), 3.42 (3H, s, OCH$_3$), 3.49 (1H, m, 24″-H), 3.72 (1H, m, 1-H), 3.86 (1H, m, 3-H), 4.60 and 4.75 (2H, each d, J=7Hz, OCH$_2$O), 4.68 (2H, s, OCH$_2$O), 5.55 (1H, m, 6-H), 6.75 (1H, br., OH), 7.43 and 7.84 (4H, each d, J=9Hz, aromatic)

IR (neat): 3320 cm$^{-1}$

Elementary analysis for C$_{40}$H$_{58}$O$_7$SF$_6$: Calcd. (%): C,60.28; H,7.34 Found (%): C,60,05; H,7.41

Example 16

Preparation of 1α,3β-bis(methoxymethoxy)-24,24-dihomo-26,26,26,27,27,27-hexafluoro-25-hydroxy-cholest-5-ene (Compound XX):

The compound (XIX) obtained in Example 15 (1.4 g, 1.8 mmol) is dissolved in a mixture of THF (12 ml) and methanol (12 ml), and to the mixture is added dipotassium hydrogen phosphate (1.1 g) and 5% sodium-amalgam (5.0 g), and the mixture is stirred at room temperature for 2.5 hours. The insoluble substances are filtered off, and the filtrate is diluted with ethyl acetate, washed with saline solution and dried over anhydrous sodium sulfate. After distilling off the solvent, the residue is purified by silica gel column chromatography (eluant, hexane-ethyl acetate=8:1) to give the title compound (XX) (831 mg, 73%).

$^1$H-NMR (CDCl$_3$) δ: 0.69 (3H, s, 18-H), 0.92 (3H, d, J=6Hz, 21-H), 1.02 (3H, s, 19-H), 3.35 (3H, s, OCH$_3$), 3.39 (3H, s, OCH$_3$), 3.73 (1H, m, 1-H), 3.86 (1H, m, 3-H), 4.30 (1H, br., OH), 4.58 and 4.73 (2H, each d, J=7Hz, OCH$_2$O), 4.66 (2H, s, OCH$_2$O), 5.56 (1H, m, 6-H)

IR (neat): 3290 cm$^{-1}$

Elementary analysis for C$_{33}$H$_{50}$O$_5$F$_6$: Calcd. (%): C,61.66; H,8.16 Found (%): C,61,62; H,8.02

Example 17

Preparation of 24,24-dihomo-26,26,26,27,27,27-hexafluoro-1α,3β,25-trihydroxy-cholest-5-ene (Compound XXI):

To the compound (XX) obtained in Example 16 (830 mg, 1.3 mmol) are added THF (10 ml) and 6N hydrochloric acid (2 ml), and the mixture is stirred at 50° C. for 6 hours. The reaction mixture is diluted with ethyl acetate, washed with saturated sodium hydrogen carbonate solution and saline solution in this order and dried over anhydrous sodium sulfate. After distilling off the solvent, the residue is purified by silica gel column chromatography (eluant, hexane-ethyl acetate=2:1) to give the title compound (XXI) (531 mg, 74%). M.p. 189°-191° C. (recrystallized from acetone-hexane)

$^1$H-NMR (CDCl$_3$) δ: 0.68 (3H, s, 18-H), 0.92 (3H, d, J=6Hz, 21-H), 1.03 (3H, s, 19-H), 3.84 (1H, m, 1-H), 3.98 (1H, m, 3-H), 5.59 (1H, m, 6-H)

IR (neat): 3500, 3320 cm$^{-1}$

Elementary analysis for C$_{29}$H$_{44}$O$_3$F$_6$: Calcd. (%): C,54.19; H,6.90 Found (%): C,54,30; H,7.00

Example 18

Preparation of 1α,3β-diacetoxy-24,24-dihomo-26,26,26,27,27,27-hexafluoro-25-hydroxy-cholest-5-ene (Compound XXII):

The compound (XXI) obtained in Example 17 (472 mg, 0.85 mmol) is dissolved in pyridine (2 ml), and thereto is added acetic anhydride (0.4 ml), and the mixture is stirred at room temperature for 2 days. After adding a piece of ice, the mixture is stirred for 10 minutes and extracted with ethyl acetate. The organic layer is washed with 2N hydrochloric acid, saturated sodium hydrogen carbonate solution and saline solution in this order and dried over anhydrous sodium sulfate. After distilling off the solvent, the residue is purified by silica gel column chromatography (eluant, hexane-ethyl acetate=9:1) to give the title compound (XXII) (192 mg, 35%). M.p. 121°–123° C. (recrystallized from hexane-ethyl acetate)

$^1$H-NMR (CDCl$_3$) δ: 0.67 (3H, s, 18-H), 0.90 (3H, d, J=6Hz, 21-H), 1.10 (3H, s, 19-H), 2.04 (3H, s, COCH$_3$), 2.07 (3H, s, COCH$_3$), 3.38 (3H, s, OH), 4.91 (1H, m, 3-H), 5.05 (1H, m, 1-H), 5.52 (1H, m, 6-H)

IR (neat): 3300, 1730 cm$^{-1}$

Elementary analysis for C$_{33}$H$_{48}$O$_5$F$_6$: Calcd. (%): C,62.05; H,7.58 Found (%): C,61,89; H,7.39

Example 19

Preparation of the 24,24-dihomo-26,26,26,27,27,27-hexafluoro-1α,3β,25-trihydroxy-cholesta-5,7-diene (Compound IId):

The compound (XXII) obtained in Example 18 (119 mg, 0.18 mmol) is dissolved in carbon tetrachloride (2 ml), and thereto is added N-bromosuccinimide (46.2 mg, 1.4 equivalent), and the mixture is refluxed under argon gas for 20 minutes. The reaction mixture is ice-cooled and the insoluble substances are filtered off. After the filtrate is distilled to remove the solvent, the residue is dissolved in THF (5 ml) and thereto is added a catalytic amount of tetra-n-butylammonium bromide. The mixture is stirred in a dark room at room temperature under argon gas for one hour. After adding further tetra-n-butylammonium fluoride (0.65 ml, as 1M solution in THF, 3.5 equivalents), the mixture is again stirred for 30 minutes. [This mixture contains the diene compound (IIc) and it can be isolated by a conventional method in a yield of 192 mg (35%)]. The above reaction mixture is diluted with ethyl acetate, washed with saturated sodium hydrogen carbonate solution and saline solution in this order, and dried over anhydrous sodium sulfate. After distilling off the solvent, the residue is dissolved in THF (5 ml) and thereto is added 5% potassium hydroxide-methanol (2 ml). The mixture is stirred at room temperature under argon gas overnight. The reaction mixture is diluted with ethyl acetate, washed with saline solution and dried over anhydrous sodium sulfate. After distilling off the solvent, the residue is purified by silica gel column chromatography (eluant, hexane-ethyl acetate=2:1) to give the title compound (IId) (19.1 mg, 20%).

UV λ$_{max}$: 294, 282, 272 nm $^1$H-NMR (CDCl$_3$) δ: 0.66 (3H, s, 18-H), 0.83 (3H, s, 19-H), 0.91 (3H, d, J=6Hz, 21-H), 3.67 (1H, m, 1-H), 3.91 (1H, m, 3-H), 5.32 and 5.58 (2H, m, 6- and 7-H)

Example 20

Preparation of 24,24-dihomo-1α,25-dihydroxy-26,26,26,27,27,27-hexafluoro-vitamin D$_3$ (Compound IV, n=5):

The compound (IId) obtained in Example 19 (19 mg, 0.03 mmol) is dissolved in a mixture of benzene (90 ml) and ethanol (40 ml), and the mixture is irradiated with ultraviolet by means of medium-pressure mercury lamp (Hanovia 654A, 200 W) at 0° C. under argon gas for 5 minutes. The solution is refluxed under argon gas for one hour. After distilling off the solvent, the residue is purified by thin layer chromatography (developer, benzene-ethyl acetate=3:1, four times developing, Rf=0.39) to give the title compound (IV) (0.452 mg, 2.3%).

UV λ$_{max}$: 265 nm, λ$_{min}$: 228 nm $^1$H-NMR (CDCl$_3$) δ: 0.54 (3H, s, 18-H), 0.92 (3H, d, J=6Hz, 21-H), 2.34 (1H, dd, J=13Hz and 7Hz, 4β-H), 2.58 (1H, dd, J=13Hz and 4Hz, 4α-H), 2.85 (1H, dd, J=12Hz and 3Hz, 9β-H), 4.20 (1H, m, 3-H), 4.42 (1H, m, 1-H), 5.00 (1H, br.s, 19E-H), 5.35 (1H, br.s, 19Z-H), 6.02 (1H, d, J=11Hz, 7-H), 6.36 (1H, d, J=11Hz, 6-H)

Experiment

Test method:

Subculture cells (HT-29) derived from human colonic cancer were inoculated onto a 24-well plate for tissue culture and thereto was added calf serum in an amount of 100% by weight, which was cultured in RPMI-1640 medium. After culturing for about 24 hours, the supernatant was removed. To the residue was added a medium containing 2×10$^{-3}$M sodium butyrate and 1α,25-dihydroxyvitamin D$_3$ or a vitamin D$_3$ analogue of this invention (exchange of the medium), and the mixture was subjected to stationary culture in a culture vessel containing carbon dioxide (5% CO$_2$ - 95% air) at 37° C. On every other day, the culture medium was exchanged with the same medium as mentioned above, and on 7th day, the number of the myxopoietic cells and shape of the cells were observed by the method of Augeron et al. [cf. Cancer Res, Vol. 44, 3961, 1984].

It is known that the myxopoiesis is observed in normal cells of large intestine (the colon) but not in cancerous cells. Accordingly, as a marker for measuring the fact that the cancer cells HT-29 was differentiated and could express the characteristic of normal cells, the number of mycopoietic cells was measured.

Results:

The data obtained above were shown in percentage based on whole cells (200 cells) measured. The results are shown in the following Table 1.

TABLE 1

| Test compound | Concentration (M) | Number of myxopoietic cells (%) |
|---|---|---|
| Non | 0 | 19 ± 3 |
| 1α,25-dihydroxy-vitamin D$_3$ | 10$^{-7}$ | 86 ± 5 |
| 1α,25-dihydroxy-vitamin D$_3$ | 10$^{-8}$ | 37 ± 0 |
| Compound A | 10$^{-7}$ | 100 |
| Compound A | 10$^{-8}$ | 91 ± 1 |
| Compound A | 10$^{-9}$ | 52 ± 7 |
| Compound B | 10$^{-7}$ | 96 ± 5 |
| Compound B | 10$^{-8}$ | 45 ± 11 |
| Compound B | 10$^{-9}$ | 16 ± 6 |

As is clear from the above results, when the HT-29 cells were treated by 2×10$^{-3}$M sodium butyrate and the compounds of this invention, the cells were differentiated into myxopoietic cells.

What is claimed is:

1. A fluorine-containing vitamin D$_3$ analogue of the formula [I]:

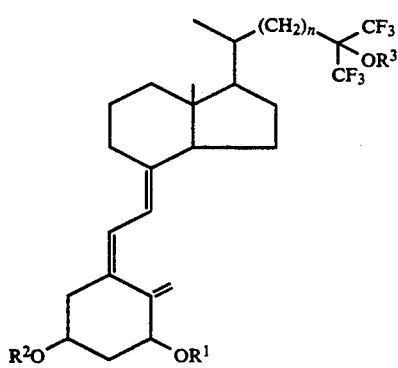

wherein $R^1$, $R^2$ and $R^3$ are independently a hydrogen atom, a chemically inactive hydroxy-protecting group, an acyl having 2 to 8 carbon atoms, or an alkyl having 1 to 8 carbon atoms, and n is an integer of 4 to 6.

2. The compound according to claim 1, wherein $R^1$, $R^2$ and $R^3$ are all hydrogen atoms and n is an integer of 4 to 5.

3. A pharmaceutical composition for inducing cell differentiation which comprises as an active ingredient an effective amount of the compound as set forth in claim 1 in admixture with a conventional pharmaceutically acceptable carrier or diluent.

4. The composition according to claim 3, wherein the active compound is the compound as set forth in claim 2.

5. The compound according to claim 1 which is a member selected from the group consisting of "24-homo-26,26,26,27,27,27-hexafluoro-1α,25-dihydroxyvitamin $D_3$"

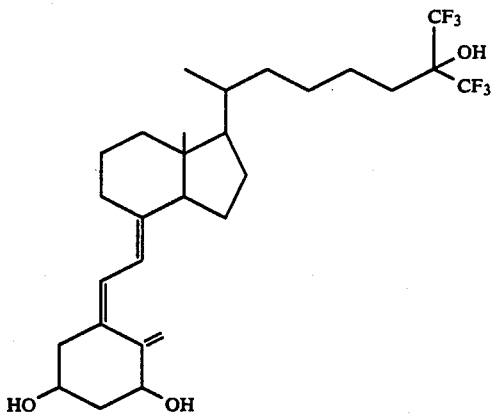

"24,24-bishomo-26,26,26,27,27,27-hexafluoro-1α,25-dihydroxyvitamin $D_3$"

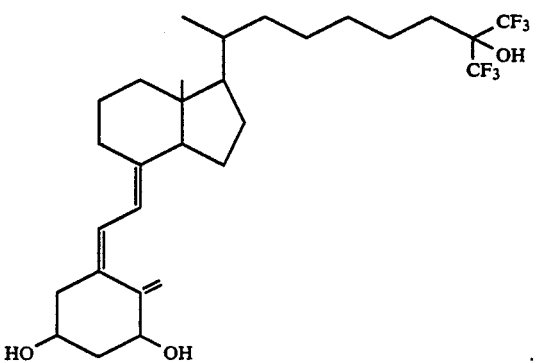

* * * * *